(12) United States Patent
Cunningham

(10) Patent No.: US 6,916,313 B2
(45) Date of Patent: Jul. 12, 2005

(54) CATHETER ASSEMBLY WITH JOINABLE CATHETERS

(75) Inventor: Jon Cunningham, Cumming, GA (US)

(73) Assignee: Medically Advanced Design, LLC, Cumming, GA (US)

( * ) Notice: Subject to any disclaimer, the term of this patent is extended or adjusted under 35 U.S.C. 154(b) by 129 days.

(21) Appl. No.: 10/287,566

(22) Filed: Nov. 4, 2002

(65) Prior Publication Data

US 2004/0087892 A1 May 6, 2004

(51) Int. Cl.[7] .............................................. A61M 25/16
(52) U.S. Cl. ........................ 604/533; 604/43; 604/523
(58) Field of Search .............................. 604/533, 96.01, 604/43, 532, 534, 535, 538, 27, 103, 103.03, 103.04, 106, 164.05, 180, 18, 513, 284; 138/115, 117

(56) References Cited

U.S. PATENT DOCUMENTS

| 5,415,639 A | * | 5/1995 | VandenEinde et al. ...... 604/528 |
| 5,947,953 A | | 9/1999 | Ash |
| 6,001,079 A | | 12/1999 | Pourchez |
| 6,190,349 B1 | | 2/2001 | Ash |

* cited by examiner

*Primary Examiner*—Kevin C. Sirmons
(74) *Attorney, Agent, or Firm*—Technoprop Colton LLC

(57) ABSTRACT

A multiple lumen catheter assembly having at least two catheters separate and independent from each other along at least a portion of their lengths, and that can be selectively joined together to change the separation distances between the catheters by of a connecting means.

17 Claims, 6 Drawing Sheets

CATHETER ASSEMBLY WITH JOINABLE CATHETERS

BACKGROUND OF THE INVENTION

1. Technical Field.

The present invention relates generally to the field of catheters for use in applications that require blood, fluids, medicated solutions, and other solutions to be removed from and introduced into a person. More particularly, the present invention relates to catheters having dual or multiple independent catheters in which a practitioner can control the distance of separation between the lumens at the distal end of the catheter.

2. Prior Art.

Hemodialysis, one procedure that requires the introduction and removal of blood from a patient, is a routine treatment for patients with renal failure. When patients are placed on hemodialysis, such patients require the placement of a catheter into a large blood vessel through a subcutaneous tunnel. In conventional procedures including the Seldinger technique, the catheter is inserted into the patient's blood vessel. This catheter, termed a hemodialysis catheter, is connected to a hemodialysis machine and is the vital connection between the patient and the hemodialysis unit. Once the practitioner has properly inserted the hemodialysis catheter into the patient, reliable hemodialysis can be performed for weeks to months using the placed catheter.

U.S. Pat. Nos. 6,190,349 and 5,947,953 to Ash et al. disclose a multiple catheter assembly and methods for inserting the same, in which first and second catheters are connected by a splittable membrane. The catheter assemblies in Ash '349 and Ash '953 comprise at least two independent catheters that are splittable to a length not predetermined by the catheter assembly. As the catheter assemblies in Ash '349 and Ash '953 are splittable as such, it may be possible to split or separate the catheters from each other within the assembly substantially beyond a desired or desirable length, which in some cases can impair the function of the catheter assembly. The thinness of the membrane initially holding the two lumens to each other makes this a likely possibility. Similarly, once the Ash '349 and Ash '953 lumens are split from each other, they cannot be reattached to each other.

U.S. Pat. No. 6,001,079 to Pourchez discloses a multilumen catheter comprising two lumens defined by a single wall for guiding a fluid. The Pourchez '079 catheter is for the circulation of at least one fluid between a patient's body cavity or vessel and a fluid circulating means. Although the Pourchez '079 catheter has separated catheter lumen tips, the distance between the lumen tips is predetermined and is not adjustable. Further, the unseparated portion of the lumens of the Pourchez '079 catheter are joined together and are not independent as they share a common wall. As the Pourchez '079 catheter has a set separation distance between the two lumens, which cannot be changed, the Pourchez '079 catheter may not be useful for a wide variety of sizes of patients.

Accordingly, there is a need for an improved catheter, more particularly a hemodialysis catheter with improved stability and performance. Further, there is a need for a catheter that can remain within a patients with less chest discomfort. It is to this and other needs that the present invention is directed.

BRIEF SUMMARY OF THE INVENTION

The present invention includes a catheter assembly with multiple joinable catheters such that the distance between the two catheters at distal ends of the catheters can be varied. While the invention is described herein in conjunction with the preferred and illustrative embodiments, it will be understood that the invention is not limited to these embodiments.

The catheter assembly of the present invention is intended for use in applications in which bodily fluids, medicated solutions, and other solutions are introduced into and/or removed from the body. For example, in the case of hemodialysis treatment, one embodiment of the invention is useful for the removal of blood from a patient for purification and for reintroducing the blood into the patient after purification through the same blood vessel. In such applications, the catheter assembly can be used in many blood vessels including the femoral blood vessels, subclavian blood vessels or other blood vessels.

The catheters of the present invention have two ends that have distinctive functions. More particularly, a distal end of each catheter is adapted to extend within the patient and a proximal end, opposite the distal end, of each catheter is adapted to remain outside the patient's body for cooperating with a means for treating or purifying the fluids drawn from the patient.

In one embodiment, the catheter assembly has at least two catheters that are approximately parallel to one another. The at least two catheters are long enough to extend though the subcutaneous tunnel from the exit site to the catheterized blood vessel. The at least two catheters are formed from two independent tubular structures. Each tubular structure has a relatively constant wall thickness and flow cross-section across its length and is used for facilitating simultaneous opposing fluid flow between the patient and an exterior unit, for example, a hemodialysis unit. Further, as the catheter assembly can be within the patient for a significant period of time, each catheter is sufficiently flexible to avoid discomfort, trauma, or stenosis to the patient.

The at least two catheters of the catheter assembly are joinable at sections along the walls of the at least two catheters towards the distal end of the catheter. These sections may be pre-selected or non-preselected distances. In one embodiment, the catheters are joinable at pre-selected positions on generally opposite flat facing surfaces of each of the at least two catheters. As more sections of the catheters are joined, the distance between the distal tips of the catheters is decreased. In many cases, the joining of sections of the at least two catheters allows the practitioner to control the distance between the tips at the distal ends of the catheters, which can be used to maximize the fluid flow and the comfort to the patient.

The means for joining the catheters of the catheter assembly can be numerous. An illustrative example includes a joining means such as a series of interlocking junctions, in which the elements of each locking junction cooperate with each other to lock the at least two lumens together. Another illustrative example includes the use of an adhesive placed along the facing walls of the catheters so that the at least two catheters can be joined by pressing the facing walls of the respective catheters together.

The joinable tip configuration of the catheter assembly allows the at least two catheters to be spaced apart from one another a selected distance without compromising the structure and structural integrity of each of the at least two catheters. This ability to change the spacing between the at least two catheters can allow the practitioner to adjust the catheter assembly to fit different patients without affecting the function of the catheter assembly. In a hemodialysis application, this spacing can help to prevent mixing of the cleansed blood, which returns through one of the at least two catheters, and the blood being removed from the blood vessel, which leaves through another one of the at least two catheters.

In operation and use, the catheter assembly can be used for the removal of fluid to be purified from the patient and/or subsequently for the reintroduction of purified fluid into patient. Initially, the at least two catheters are supplied separated from each other along the length of the at least two catheters an amount equal to or preferably greater than the maximum distance recommended for the specific procedure. Before, after or during the installation of the catheter assembly, the practitioner then can join the at least two catheters together along the facing walls of the at least two catheters using the joinable means to reduce the separation distance to the desired or required distance. In one example, after the joining of the at least two catheters as necessary, the catheter assembly can be installed into a patient by ordinary medical techniques, after which the catheter assembly can perform its function. In another example, such as in the case of hemodialysis, after the at least two catheters have been joined and inserted through the patient's skin into the appropriate blood vessel (by techniques such as the Seldinger technique), blood is channeled out of the patient through one lumen of the at least two catheters to a purification machine and after purification the blood is channeled back into the patient through another of the at least two catheters.

Although embodiments of the present invention are generally disclosed in the context of hemodialysis catheters, it is understood that such embodiments can be applied to other catheters that are used for procedures that require that fluid, blood, medicated solution, or other solutions be removed and introduced into a patient. Such procedures include, but are not limited to, hemodialysis, perfusion, chemotherapy, and plasmapheresis.

These features and advantages of the present invention and the complementary method for installation and use of the invention will become more apparent to those of ordinary skill in the art when the following detailed description of the preferred embodiments is read in conjunction with the appended figures, in which like reference numerals represent like components throughout the various figures.

DETAILED DESCRIPTION OF THE PREFERRED EMBODIMENTS

Illustrative embodiments of the present invention include multiple lumen catheter assembly 10 that has at least two joinable catheters 12, 14 such that the distance between two of the at least two catheters 12, 14 at a distal section or end 20 of the catheter assembly 10 can be varied. While the invention is described herein in conjunction with the preferred and illustrative embodiments, it will be understood that the invention is not limited to these embodiments.

Figure 1:
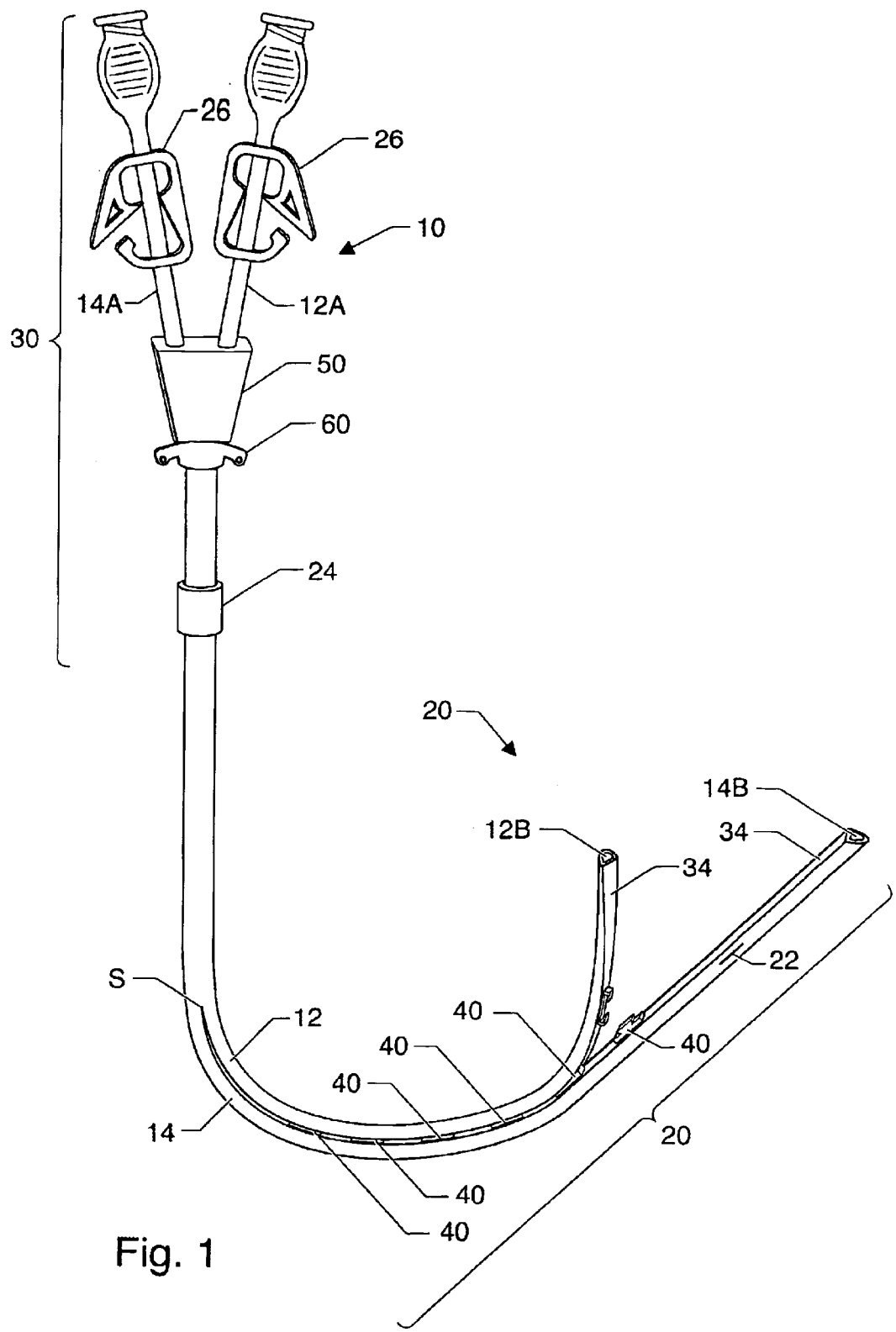
FIG. 1 is a perspective view of one illustrative embodiment of the present invention.
Figure 2:
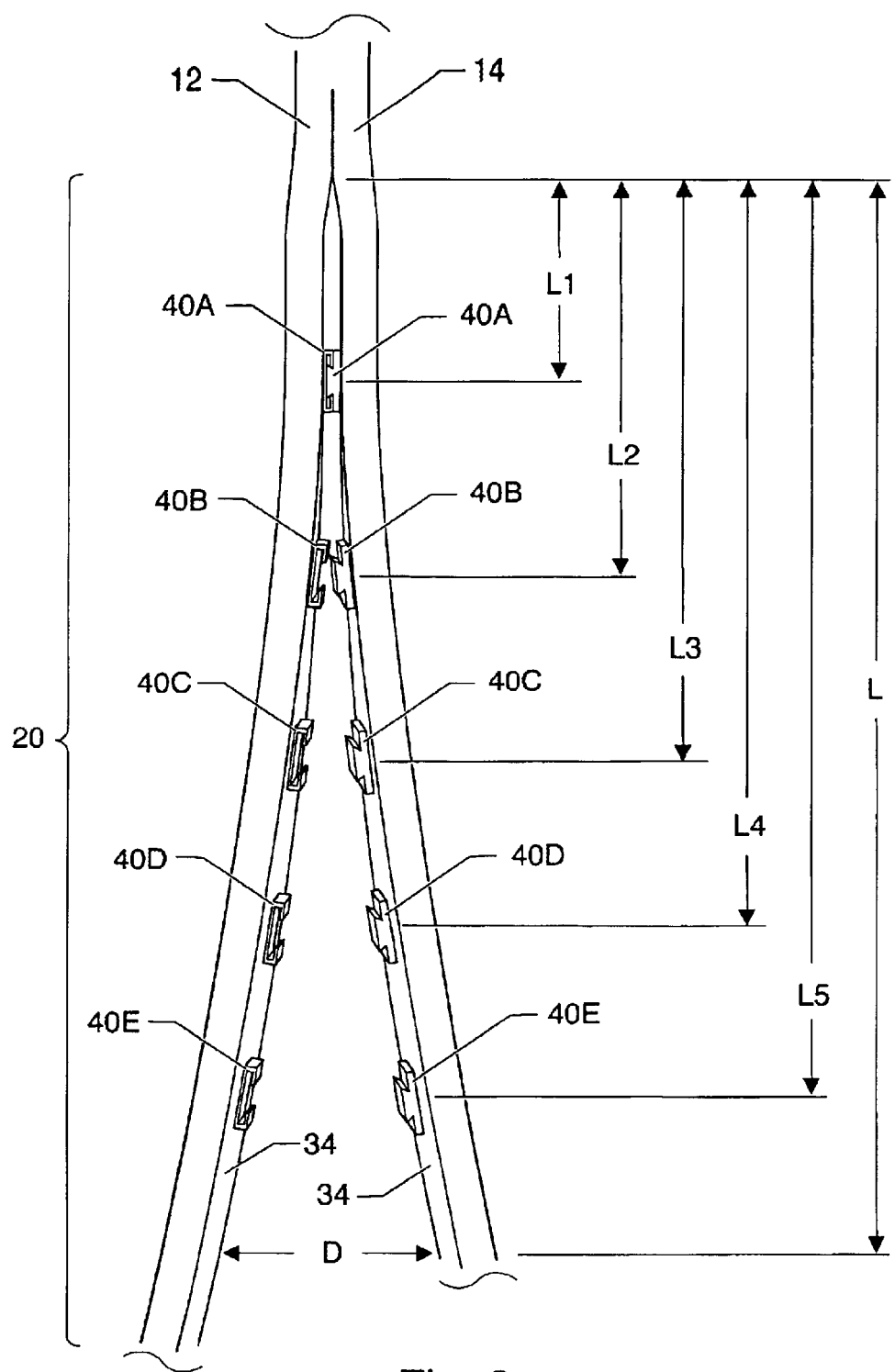
FIG. 2 is a perspective view of the distal end of the embodiment shown in FIG.1.
Figure 3A:
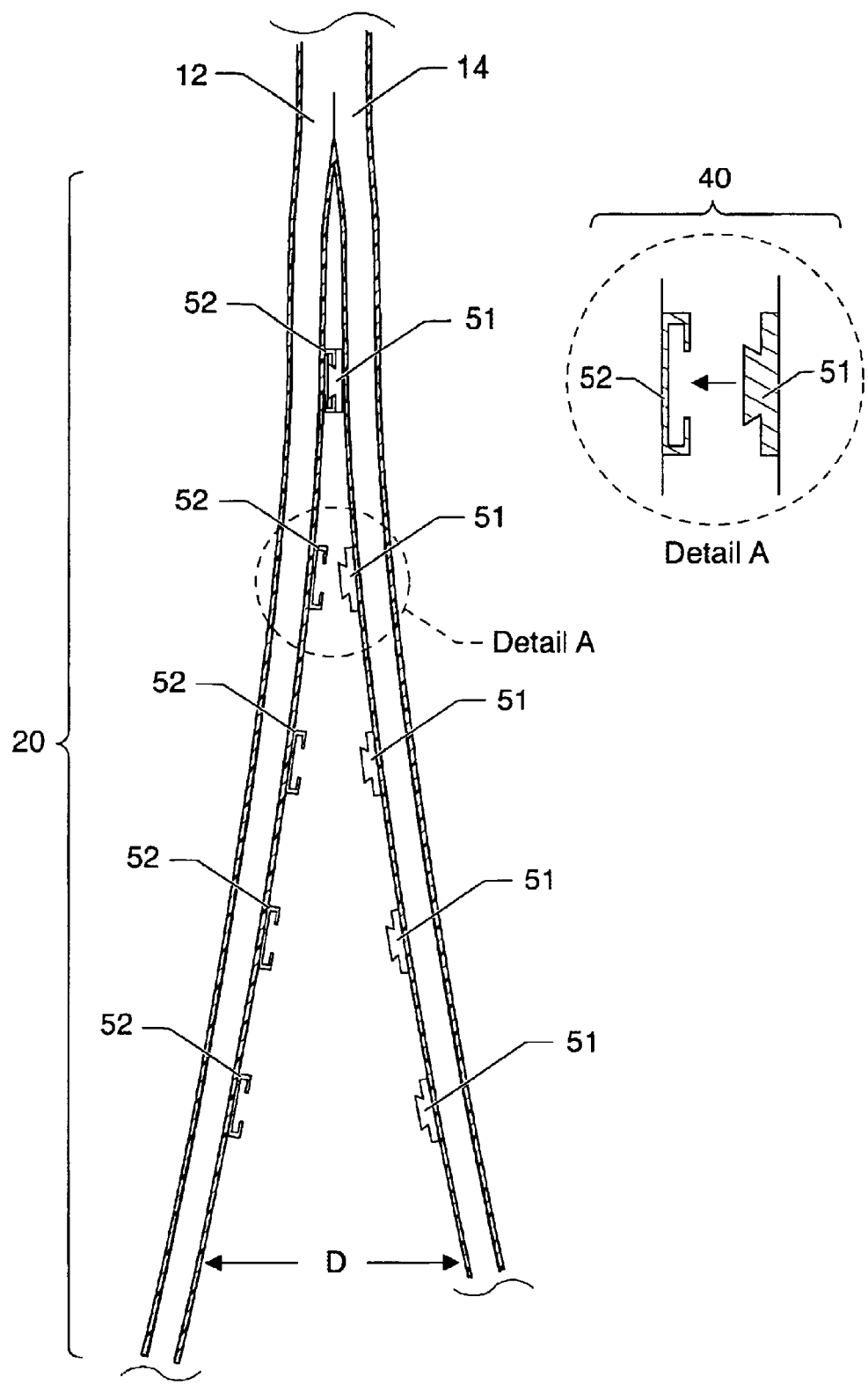
FIG. 3 is a perspective view of the distal end of a second illustrative embodiment of the present invention.
Figure 3B:
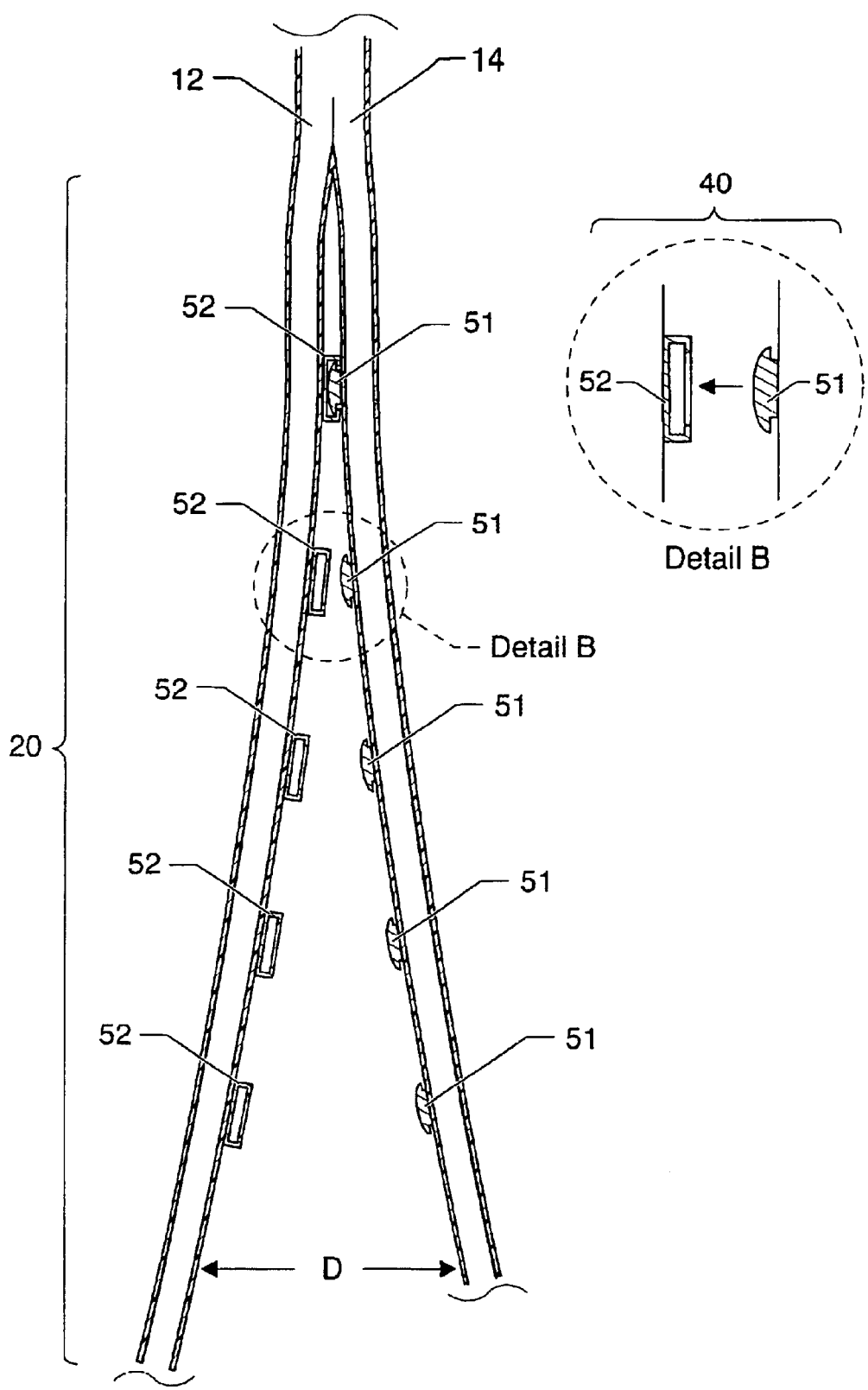
Figure 4:
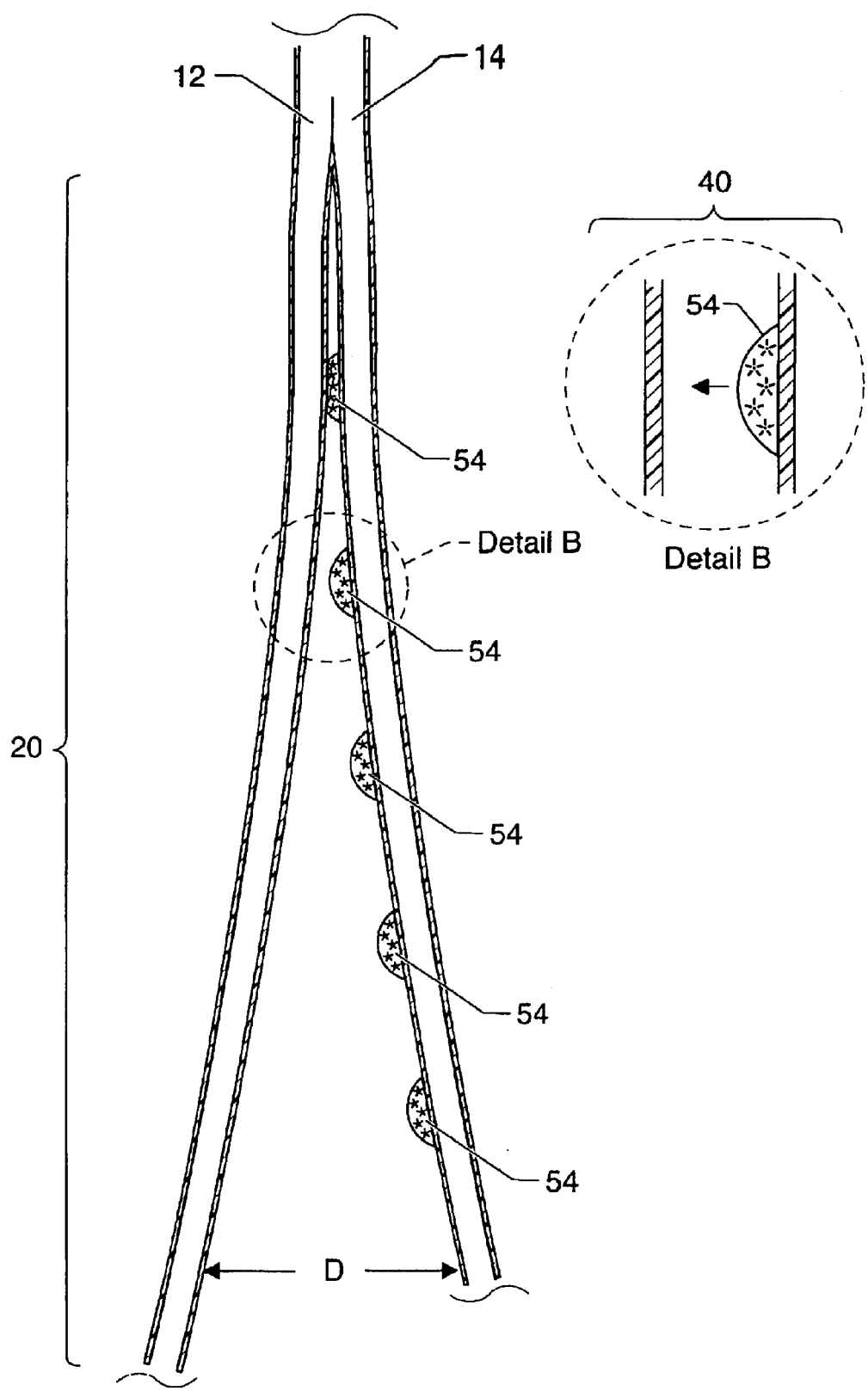
FIG. 4 is perspective view of the distal end of a third illustrative embodiment of the present invention.
Figure 5:
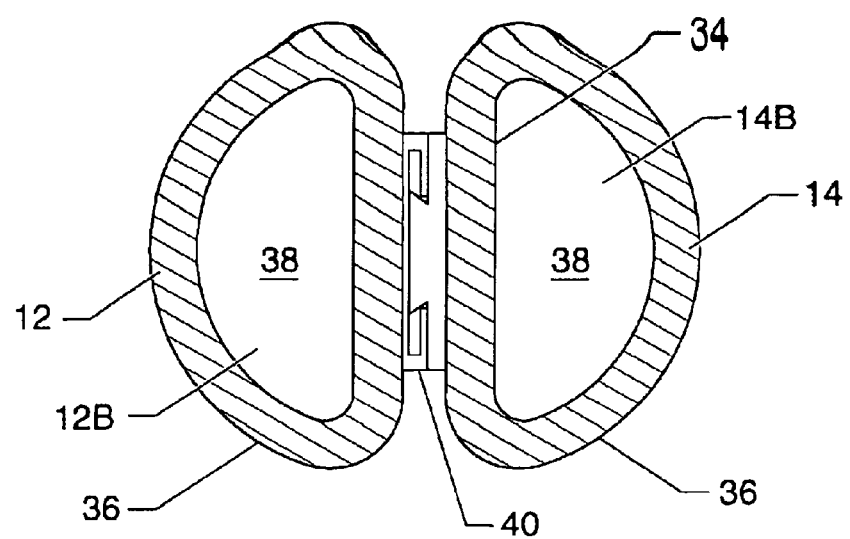
FIG. 5 is a cross section along line 5—5' of the embodiment shown in FIG. 1.
Figure 6:
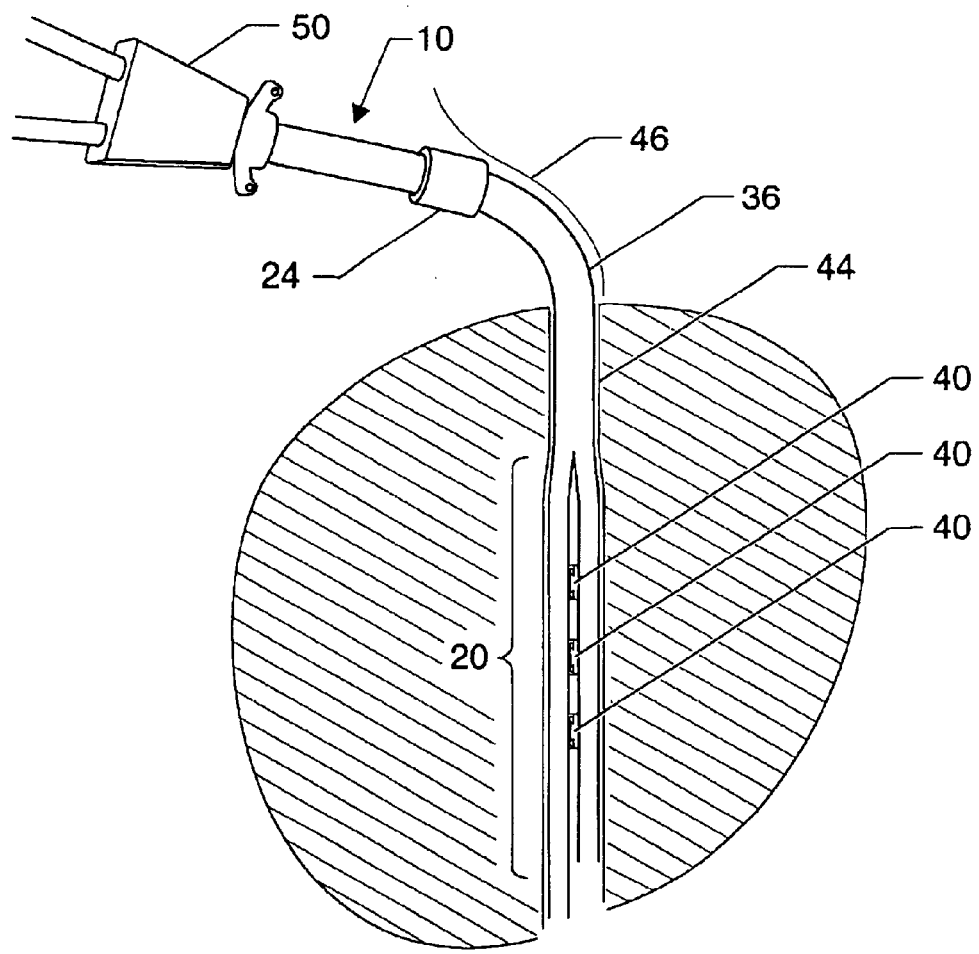
FIG. 6 is a sectional view of a body with the embodiment shown in FIG. 1 placed therein.

Catheter assembly 10 comprising multiple catheters 12, 14 can be constructed in accordance with the illustrative embodiments of the present invention as shown in FIGS. 1–6. FIG. 1 is a perspective view of catheter assembly 10 showing the general structure of the one illustrative embodiment in an unstressed configuration. FIG. 2 is a perspective view of a distal section 20 of the embodiment of shown in FIG. 1 showing generally the joinable catheters configuration. FIG. 3 is a perspective view of a distal section 20 of another illustrative embodiment showing one means for providing the joinable catheters configuration. FIG. 4 is a perspective view of a distal end 20 of the embodiment another illustrative embodiment showing another means for providing the joinable catheters configuration. FIG. 5 is a cross-section of the embodiment shown in FIG. 1 along line 5–5'. FIG. 6 is a sectional view of the embodiment shown in FIG. 1 within the body of a patient.

Catheter assembly 10 is intended for use in applications in which bodily fluids, medicated solutions, and other solutions are introduced into and removed from the body. For example, in the case of hemodialysis treatment, one embodiment of the invention is useful for the removal of blood from a patient's blood vessel for purification and for reintroducing the blood into the patient after purification through the same blood vessel. In such applications, catheter assembly 10 can be used in many blood vessels including the femoral blood vessels, subclavian blood vessels or other blood vessels.

Referring now to FIGS. 1 and 6, catheter assembly 10 has two ends with distinctive functions. More particularly, a distal end 20 of catheter assembly 10 is adapted to extend within a blood vessel 44 of a patient and a proximal end 30, opposite the distal end 20, of catheter assembly 10 is adapted to remain outside the patient's body for cooperating with a means for exchanging fluids drawn from the blood vessel 44. Preferable, the at least two catheters 12, 14 are approximately parallel to one another and are long enough to extend though the subcutaneous tunnel 46 from the exit site to the catheterized blood vessel 44.

The at least two lumens 12B,14B of the respective catheters 12, 14 are formed from two independent tubular structures. Each tubular structure has a relatively constant wall thickness and flow cross-section across its length and is used for facilitating simultaneous opposing fluid flow between the patient and an exterior unit, for example a hemodialysis unit, and back to the patient. Each of the at least two catheters 12, 14 is preferably constructed of a material of a sufficient rigidity to maintain its general shape under normal usage, including instances when negative pressure is applied to catheter assembly 10 (for example when aspirating blood from blood vessel 44) or when positive pressure is applied to the catheter assembly 10 (for example when introducing blood to the blood vessel 44). Preferably, as catheter assembly 10 can be within the patient for a significant period of time, each of the at least two catheters 12, 14 also is sufficiently flexible to avoid discomfort, trauma, or stenosis to the patient.

As shown in FIG. 2, the at least two catheters 12, 14 of catheter assembly 10 are joinable to each other at at least one position along a region towards the distal end 20 of catheter assembly 10. Preferably, the at least two catheters 12, 14 are joinable at pre-selected points generally along the facing flat walls 34 of each of the at least two catheters 12, 14 through joining at least one connecting means 40. The joining of more portions of the at least two catheters 12, 14 will decrease distance D between the tips 16, 18 of the at least two catheters 12, 14, as well as the separated length L between the separated lumens catheters 12, 14.

The joining of the at least two catheters 12, 14 at at least one position allows the practitioner to control the distance D between, and the length L of separation of, the at least two catheters 12, 14 at the distal end 20. For example, if the practitioner needs the tips 16, 18 at the distal end 20 of the at least two catheters 12, 14 to be closer, the practitioner can join more sections along the walls 34 of the at least two catheters 12, 14 by using connecting means 40. Contrastingly, if the practitioner wants to maintain an increased distance D and/or length L at the distal end 20 between the at least two catheters 12, 14, the practitioner will not join as many sections of the least two catheters 12, 14. Preferably, once the at least two catheters 12, 14 are joined, the catheters 12, 14 cannot be separated without applying an undue force and/or destroying the structural integrity of the catheters 12, 14. In this manner, the practitioner generally can be assured that the catheters 12, 14 will not separate within the patient's body.

There can be any number of connecting means 40 located along the facing walls 34 of the at least two catheters 12, 14. However, for ease of use, and to decrease the number of possible clotting or coagulation sites, the use of one or two connecting means 40 is preferred. Five such connecting means 40 are shown in FIG. 2 that allow the joining of the at least two catheters 12, 14 at several different lengths L. Specifically, joining connecting means 40A results in a catheter separation distance of L1, joining connecting means 40B results in a catheter separation distance of L2, joining connecting means 40C results in a catheter separation distance L3, joining connecting means 40D results in a catheter separation distance of L4, joining connecting means 40E results in a catheter separation distance of L5, and so on. Generally, if an outer connecting means such as, for example, connecting means 40C is joined, all intervening connecting means 40 such as connecting means 40B and 40A also are joined.

Referring to FIG. 3A–3B, in one embodiment the at least two catheters 12, 14 are joinable by connecting means 40 that can be a series of interlocking junctions. In this embodiment, the elements of each interlocking junction cooperate with each other to lock sections of the at least two catheters 12, 14 together. More particularly, as interlocking junctions can have one male element 51 and one female element 52, the practitioner can selectively join or snap sections of the at least two catheters 12, 14 together using male element 51 and female element 52. Preferably, once each of the connecting means 40 is locked together, male element 51 and female element 52 cannot be separated without applying an undue or destructive force to the at least two catheters 12, 14, as discussed previously, to help prevent undesirable separation of the catheters 12, 14.

Referring to FIG. 4, another embodiment of connecting means 40 is through the use of adhesive 54. Such adhesive 54 can be a natural or synthetic adhesive. In this embodiment, the adhesive 54 preferably is preferably is pre-positioned at certain intervals along at least one of the walls 34 of the at least two catheters 12, 14 and the practitioner uses the adhesive 54 to join the catheters 12, 14. Alternatively, the adhesive 54 can be along the entire wall 34 of at least one or two of the at least two catheters 12, 14, such that the adhesive 54 on one wall 34 interacts with the adhesive 54 on another wall 34, creating a tighter bond.

Other alternatives can be used. For example, a locking zipper-type seal, such as a variation on the zipper on plastic storage bags, can be used. One of ordinary skill in the medical device sealing field can substitute various different locking means for the disclosed means without undue experimentation.

As shown in FIG. 5, the at least two lumens 12B, 14B each preferably have an approximately semi-circular or "D"-shaped cross section. The connecting means 40 does not affect the cross sectional shape or interior dimensions or flow pattern of the at least two lumens 12B, 14B. More specifically, as is known in the catheter art, each catheter 12, 14 has an inner peripheral surface wall 36 defining the interior flow cavity 38 of the lumens 12B, 14B. When using two catheters, as shown as the illustrative example in the FIGs., as the catheters 12, 14 generally run parallel to each other, the generally flatter side surface walls 34 are close to and facing one another. The connecting means 40 preferably are located on the flatter side surface walls 34 of each catheter 12, 14. As shown, the connecting means 40 does not impact the size or shape of the at least two lumens 12B, 14B.

It is understood that the generally semi-circular cross section is for illustrative purposes. For example, the cross section of catheter assembly 10 can be shaped as an oval, ellipse, square, triangle, kidney bean, or other shapes. Further, it should be understood that the catheters may be further subdivided and/or additional catheter tubes of the same or varied cross sectional configurations can be provided within the scope of the invention. A person of ordinary skill in the art can select and configure catheter assembly 10 with such shapes without undue experimentation.

Referring back to FIG. 1, the at least two catheters 12, 14 can be separate or independent from each other starting at many different points. As shown in FIG. 1, the two catheters 12, 14 shown are part of a generally unitary double catheter structure for approximately half their total length, or until spliting point S. Splitting point S can be at any selected distance from connecting hub 50, but preferably should be at a maximum distance so as to allow catheters 12, 14 to be separate and independent from each other for a medically appropriate distance. For example, the medically appropriate distance for a hemodialysis catheter can be the maximum desirable distance for use in a human being in the 90%+size range. As such, the separated catheters 12, 14 could be used as is for larger patients (those in the 90%+size range), and the joined catheters 12, 14 could be used for smaller patients. Alternatively, splitting point S can be at the point the catheters 12, 14 leave the connecting hub 50, meaning that catheters 12, 14 are separate and independent along their entire lengths from connecting hub 50.

As shown, the independence of the at least two catheters 12, 14 can confer several benefits to catheter assembly 10. The distinct surface walls 34 of each of the at least two catheters 12, 14 can add structural stability to catheter assembly 10. Further, as the at least two catheters 12, 14 have individual walls, it is possible to have separate lumens 12B, 14B and thus create the split tipped structure of catheter assembly 10. Importantly, the at least two catheters 12, 14 are in a free-floating configuration in the same vessel to provide higher flow rates with lower pressures and with less occlusion. The ability to change the length L of the separation and, as a result, the separation distance D, allows the use of the same catheter assembly 10 in many different sized patients.

Referring now to FIG. 6, the joinable tip structure of catheter assembly 10 allows the at least two catheters 12, 14 to be spaced apart from one another without compromising the structure of each of the at least two catheters 12, 14. This ability to change the separation distance D and length L between the at least two catheters 12, 14 allows the practitioner to adjust catheter assembly 10 to fit different patients. In a hemodialysis application, this spacing can help to prevent mixing of cleansed blood returning through one of the at least two lumens with the blood being removed from the blood vessel through another one of the at least two lumens.

Generally, larger distances D and lengths L allow for less mixing of fluids being returned with fluids being removed. However, different patients have different lengths of usable blood vessels. For example, a 6' 10" male patient typically would have a longer usable blood vessel than a 4" 8" female patient. The joinable feature of the present invention allows the practitioner to compensate for such a difference.

In addition to the joinable catheters, catheter assembly 10 can have many of the features present on conventional catheters. For example, referring back to FIG. 1, catheter assembly 10 can have a radioplaque stripe 22 for aiding in the locating of catheter assembly 10 by a fluoroscope. For another example, catheter assembly 10 can have a fabric cuff 24 that is spaced accordingly to allow for optimal and/or long-term stabilization of catheter assembly 10 in its indwelling position. For another example, catheter assembly 10 can have pair of clamps 26 that can be used to secure or close off such connector tubes before and after a procedure. Other features for optimal utilization of catheter assembly 10 are known to those with skill in the art and can be placed on catheter assembly 10 without undue experimentation.

The proximal ends 30 of the at least two catheters 12,14 can be secured to a connecting hub 50. The connecting hub 50 couples the tubular structures of the at least two catheters 12, 14 to external portions 12A, 14A of catheters 12, 14 and for communicating therewith. The connecting hub 50 can have a suturing slot 60 that can be rotatably anchored to the connecting hub 50. Such a suturing slot 60 may provide a means for stabilizing the connecting hub 50 to the patient's skin adjacent the exit site.

In operation and use, catheter assembly 10 can be used for the removal of fluid to be purified from and/or subsequently for the reintroduction of purified fluid into patient. Before, after or during the installation of catheter assembly 10, the practitioner can join the at least two catheters 12, 14 along the walls 34 of the at least two catheters 12, 14 using connecting means 40. In one embodiment, after the joining of the at least two catheters 12, 14 as necessary at the appropriate point, the catheter assembly 10 can be installed into a patient by ordinary medical techniques, after which catheter assembly 10 can perform its function. For example, in the case of hemodialysis, after catheter assembly 10 has been inserted through the patient's skin into the appropriate blood vessel 44 (by techniques such as the Seldinger technique), blood can flow out of the patient through one lumen of the at least two catheters 12, 14 to a purification machine and after purification, the blood can be channeled back into the patient through another of the two catheters 12, 14 of catheter assembly 10.

Each of the at least two catheters 12, 14 can be manufactured to have a length and width useful for catheterization of an intended blood vessel 44 and/or application. As shown, the catheters 12, 14 can be longitudinally spaced by a sufficient distance so to essentially prevent or reduce the chance for the mixing of the blood to be removed and the blood to be reintroduced. The optimal distance will vary for different applications and with the patient that will be catheterized. One of ordinary skill In the art can manufacture catheter assembly 10 without undue experimentation.

The at least two catheters 12, 14 are made from a material or materials that such is or are flexible, durable, soft, and easily conformable to the shape of the area to be catheterized and/or the subcutaneous area, and that minimize risk of harm to vessel 44 walls. If catheter assembly 10 is used for hemodialysis applications, it preferably is formed of a softer material that has a hardness of at most about 85-A on a Shore durometer scale.

The at least two catheters 12, 14 can be made of biocompatible plastics and elastomers. Such biocompatible plastics include materials such as, for example, polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as homopolymers and copolymers of polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, polyisobutylene, polymethylstyrene and other similar compounds known to those of ordinary skilled in the art. Such biocompatible elastomers include medical grade silicone rubbers, polyvinyl chloride elastomers, polyolefin homopolymeric and copolymeric elastomers, urethane-based elastomers, and natural rubber or other synthetic rubbers. One of ordinary skill in the art can select a biocompatible material suitable for manufacturing catheter assembly 10 without undue experimentation.

Although embodiments of the present invention are generally disclosed in the context of hemodialysis catheters, it is understood that such embodiments can be applied to other catheters that are used for procedures that require that fluid, blood, medicated solutions, or other solutions to be removed from and introduced into a patient. Such procedures include, but are not limited to, hemodialysis, perfusion, chemotherapy, and plasmapheresis.

The above detailed description of the preferred embodiments, examples, and the appended figures are for illustrative purposes only and are not intended to limit the scope and spirit of the invention, and its equivalents, as defined by the appended claims. One skilled in the art will recognize that many variations can be made to the invention disclosed in this specification without departing from the scope and spirit of the invention.

What is claimed is:

1. A multiple lumen catheter assembly comprising:
   a. a first catheter having a proximal end and a distal end;
   b. a second catheter having a proximal end and a distal end;
   c. a connecting means for selectively and irreversibly joining together at least a portion of the distal ends of the first and second catheters;
   wherein the first catheter and the second catheter are generally parallel; a connecting hub connects the proximal ends of the first and the second catheters; and a first fluid flow in the first catheter is in a direction different from a second fluid flow in the second catheter.

2. The catheter assembly as claimed in claim 1, wherein the catheter assembly is not split at predetermined distances from the distal end of the first catheter or the second catheter.

3. The catheter assembly claimed in claim 2, wherein the first catheter and the second catheter are selectively joinable at at least one position along generally flat side surfaces.

4. The catheter assembly claimed in claim 3, wherein the selective joining of the first catheter and second catheter decreases the distance between the first catheter and the second catheter proximal to the distal ends of the first catheter and the second catheter.

5. The catheter assembly claimed in claim 4, wherein the first catheter and the second catheter each have a generally semi-circular cross section and each comprise at least one of the generally flat side surfaces.

6. The catheter assembly claimed in claim 5, wherein the connecting means is at least one lockable junction comprising a male end and female end, wherein once the at least one lockable junction is joined together it is joined irreversibly; whereby the first catheter and the second catheter are joined selectively along a portion of the distal ends of the first catheter and the second catheter through the joining of the male end with female end.

7. The catheter assembly claimed in claim 5, wherein the first lumen catheter and the second catheter are joinable by an adhesive.

8. The catheter assembly claimed in claim 4 further comprising a third catheter.

9. A multiple lumen catheter assembly comprising:
 a. a first catheter having a proximal end and a distal end;
 b. a second catheter having a proximal end and a distal end;
 c. a connecting means for selectively and irreversibly joining together at least a portion of the distal ends of the first catheter and second catheter;
 wherein a connecting hub connects the first catheter and the second catheter at the proximal ends; a first fluid flow in the first catheter is in a direction different from a second fluid flow of the second catheter; the connecting means allows the first catheter and the second catheter to be selectively joined together at the discretion of a practitioner at a position proximal to the distal ends of the first catheter and second catheter; whereby the selective joining of the first catheter and second catheter decreases the distance between the first catheter and second catheter proximal to the distal ends of the first catheter and second catheter.

10. The catheter assembly as claimed in claim 9, wherein the first catheter and the second catheter are approximately parallel.

11. The catheter assembly as claimed in claim 10, wherein the distal end of the first catheter is longer than the distal end of the second catheter.

12. The catheter assembly as claimed in claim 11, wherein the distal end of the first catheter extends beyond the distal end of the second catheter within a patient and the first catheter is for introducing a fluid into a blood vessel in the patient and the second catheter is for removing a fluid from the blood vessel.

13. The catheter assembly as claimed in claim 12, wherein the connecting means is at least one lockable junction comprising a male end and female end, wherein once the at least one lockable junction is joined together it is joined irreversibly; whereby the first catheter and the second catheter are joined selectively along a portion of the distal ends of the first catheter and the second catheter through the joining of the male end with female end.

14. The catheter assembly as claimed in claim 13, wherein the first catheter and the second catheter cannot be joined beyond a preselected point set between the proximal end and the distal end of each of the first catheter and the second catheter.

15. The catheter assembly as claimed in claim 14, wherein the set point is at the distal end of the first catheter.

16. The catheter assembly as claimed in claim 15, wherein the catheter assembly is a hemodialysis catheter assembly.

17. The catheter assembly claimed in claim 12, wherein the first catheter and the second catheter are joinable by an adhesive.

* * * * *